United States Patent
Yang

(10) Patent No.: US 10,821,227 B2
(45) Date of Patent: Nov. 3, 2020

(54) INTRAVENOUS DRIP REAL-TIME MONITORING SYSTEM AND METHOD

(71) Applicants: Mikotek Information Inc., Taipei (TW); Ching-Wen Yang, Taipei (TW)

(72) Inventor: Ching-Wen Yang, Taipei (TW)

(73) Assignees: Mikotek Information Inc., Taipei (TW); Ching-Wen Yang, Taipei (TW)

(*) Notice: Subject to any disclaimer, the term of this patent is extended or adjusted under 35 U.S.C. 154(b) by 0 days.

(21) Appl. No.: 16/257,019

(22) Filed: Jan. 24, 2019

(65) Prior Publication Data

US 2019/0365994 A1 Dec. 5, 2019

(30) Foreign Application Priority Data

Jun. 4, 2018 (TW) .............................. 107119210 A

(51) Int. Cl.
*G08C 19/22* (2006.01)
*A61M 5/172* (2006.01)
(Continued)

(52) U.S. Cl.
CPC .............. *A61M 5/172* (2013.01); *G01G 19/14* (2013.01); *G08B 21/182* (2013.01); *G16H 20/17* (2018.01); *H04L 67/10* (2013.01); *H04Q 9/00* (2013.01); *A61M 2205/18* (2013.01); *A61M 2205/3386* (2013.01); *A61M 2205/3393* (2013.01); *A61M 2205/3553* (2013.01); *A61M 2205/3584* (2013.01); *A61M 2205/6018* (2013.01)

(58) Field of Classification Search
CPC .............. A61M 5/172; A61M 2205/18; A61M 2205/3386; A61M 2205/3393; A61M 2205/3553; A61M 2205/3584; A61M 2205/6018; G16H 20/17; G01G 19/14; G08B 21/182; H04L 67/10; H04Q 9/00
USPC ..................................................... 340/870.07
See application file for complete search history.

(56) References Cited

U.S. PATENT DOCUMENTS

2005/0065817 A1* 3/2005 Mihai .................... A61B 5/411
705/2
2006/0064053 A1* 3/2006 Bollish ............. A61M 5/16895
604/31
(Continued)

FOREIGN PATENT DOCUMENTS

CN   201469795 U  *  5/2010
CN   101954129 B  *  1/2011
(Continued)

OTHER PUBLICATIONS

The as-filed documents of U.S. Appl. No. 16/045,774, filed Jul. 26, 2018.

*Primary Examiner* — Zhen Y Wu
(74) *Attorney, Agent, or Firm* — CKC & Partners Co., LLC

(57) ABSTRACT

An intravenous drip real-time monitoring system is disclosed herein. The system includes a weight sensor, a processor and a cloud server. The weight sensor is configured to detect weight values. The processor is electrically connected to the weight sensor, is configured to calculate the weight values and when the weight values is not larger than a drip threshold, sending an alert information. The cloud server is communication connected to the processor, is configured to receive the weight values via the processor, and compare the weight values and drip setting information to calculate drip remaining time.

10 Claims, 3 Drawing Sheets

(51) Int. Cl.
*H04Q 9/00* (2006.01)
*H04L 29/08* (2006.01)
*G08B 21/18* (2006.01)
*G16H 20/17* (2018.01)
*G01G 19/14* (2006.01)

(56) References Cited

U.S. PATENT DOCUMENTS

| | | | | |
|---|---|---|---|---|
| 2011/0029324 A1* | 2/2011 | Kondo | ............ | G16H 40/20 |
| | | | | 705/3 |
| 2015/0061876 A1* | 3/2015 | Chang | ............ | A61M 5/16845 |
| | | | | 340/613 |
| 2015/0233749 A1* | 8/2015 | Wang | ............ | G08B 25/10 |
| | | | | 340/613 |
| 2015/0346013 A1* | 12/2015 | Feng | ............ | G16H 40/67 |
| | | | | 702/55 |
| 2018/0177945 A1* | 6/2018 | Sims | ............ | G01G 17/06 |

FOREIGN PATENT DOCUMENTS

| | | | | | |
|---|---|---|---|---|---|
| CN | 103656792 A | | 3/2014 | | |
| CN | 203598309 U | | 5/2014 | | |
| CN | 204352301 U | * | 5/2015 | | |
| CN | 105536105 A | | 5/2016 | | |
| CN | 107441589 A | | 12/2017 | | |
| CN | 107823754 A | | 3/2018 | | |
| CN | 104707214 A | * | 6/2018 | | |
| CN | 20150100603 A | * | 6/2018 | ............ | A61M 5/168 |
| JP | 2007-521849 A | | 8/2007 | | |
| JP | 2009-535715 A | | 10/2009 | | |
| TW | M490701 U | * | 11/2014 | ............ | H04L 12/26 |
| TW | 201606692 A | * | 2/2016 | ............ | G06Q 50/22 |
| TW | M574704 U | | 2/2019 | | |

* cited by examiner

INTRAVENOUS DRIP REAL-TIME MONITORING SYSTEM AND METHOD

RELATED APPLICATION

This application claims priority to Taiwan Application Serial Number 107119210, filed on Jun. 4, 2018, which is herein incorporated by reference.

BACKGROUND

Field of Invention

The present application relates to a real-time monitoring technology. More particularly, the present application relates to an intravenous drip real-time monitoring system and method.

Description of Related Art

Medical intravenous drip is driven by gravity mostly, the container is hanging on a stable drip stand and the liquid substance inside the container flows down naturally into intravenous. Currently, the intravenous drip is still monitoring manually, the alarm system is activated manually and required medical staffs handling while the drip ends or abnormal condition happened.

Moreover, because an intravenous drip requires individually setting according to different types and brands of drugs, therefore the drip weight monitoring also need to adjust to meet different kinds of drip. However, it will increase the inconvenience of users. In the lack of efficient monitoring, the burden on medical staff will increase. Therefore, an intravenous drip real-time monitoring system and method is required.

SUMMARY

An aspect of the disclosure is to provide an intravenous drip real-time monitoring system. The intravenous drip real-time monitoring system includes a weight sensor, a processor and a cloud server. The weight sensor is configured for detecting a weight information of a drip. The processor is electrically connected to the weight sensor. The processor is configured for calculating the weight information, and when the weight information is less than a drip threshold, the processor is configured for sending an alert information. The cloud server is communicated with the processor. The cloud server is configured for receiving the weight information transmitted from the processor, and comparing the weight information with a setting information of the drip to calculate a time remaining; wherein, the setting information comprises a weight of drip bag and the drip threshold.

Another aspect of the disclosure is to provide an intravenous drip real-time monitoring method. The intravenous drip real-time monitoring method includes operations of: detecting a weight information of a drip by a weight sensor; calculating the weight information by a processor and when the weight information is less than a drip threshold, sending an alert information by the processor; transmitting the weight information to a cloud server by the processor; and comparing the weight information with a setting information of the drip to calculate a time remaining by the cloud server; wherein, the setting information comprises a weight of drip bag and the drip threshold.

Based on aforesaid embodiments, intravenous drip real-time monitoring system and method are capable of improving the formerly intravenous drip monitoring system done by manual monitoring, utilizing the weight sensor to detect the weight of drip in real time and sending out an alert sound to caretaker remind him/her replace the drip. The intravenous drip real-time monitoring system will also send the setting information of drip from the cloud server to drip monitoring device. In some embodiments, this disclosure is able to real-time monitoring and convenient setting up the drip monitoring device.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

It will be understood that, in the description herein and throughout the claims that follow, when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Moreover, "electrically connect" or "connect" can further refer to the interoperation or interaction between two or more elements.

It will be understood that, in the description herein and throughout the claims that follow, although the terms "first," "second," etc. may be used to describe various elements, these elements should not be limited by these terms. These terms are only used to distinguish one element from another. For example, a first element could be termed a second element, and, similarly, a second element could be termed a first element, without departing from the scope of the embodiments.

It will be understood that, in the description herein and throughout the claims that follow, the terms "comprise" or "comprising," "include" or "including," "have" or "having," "contain" or "containing" and the like used herein are to be understood to be open-ended, i.e., to mean including but not limited to.

It will be understood that, in the description herein and throughout the claims that follow, the phrase "and/or" includes any and all combinations of one or more of the associated listed items.

It will be understood that, in the description herein and throughout the claims that follow, words indicating direction used in the description of the following embodiments, such as "above," "below," "left," "right," "front" and "back," are directions as they relate to the accompanying drawings.

Therefore, such words indicating direction are used for illustration and do not limit the present disclosure.

It will be understood that, in the description herein and throughout the claims that follow, unless otherwise defined, all terms (including technical and scientific terms) have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any element in a claim that does not explicitly state "means for" performing a specified function, or "step for" performing a specific function, is not to be interpreted as a "means" or "step" clause as specified in 35 U.S.C. § 112(f). In particular, the use of "step of" in the claims herein is not intended to invoke the provisions of 35 U.S.C. § 112(f).

Figure 1:
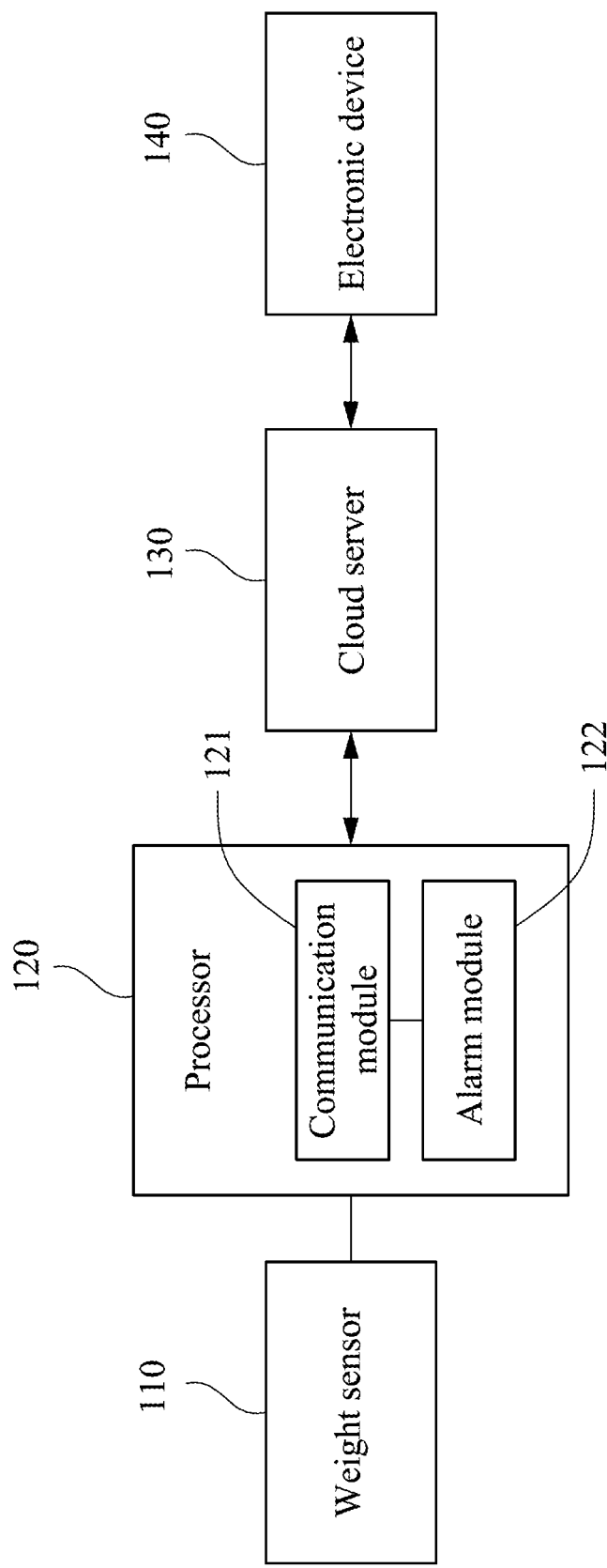
FIG. 1 is a functional block diagram illustrating an intravenous drip real-time monitoring system according to an embodiment of the disclosure.

Reference is made to FIG. 1, which is a functional block diagram illustrating an intravenous drip real-time monitoring system 100 according to an embodiment of the disclosure. As shown in FIG. 1, the system 100 includes a weight sensor 110, a processor 120, a cloud server 130 and an electronic device 140. The processor 120 includes a communication module 121 and an alarm module 122. The processor 120 is electrically connected to the weight sensor 110. The processor 120 is connected to the cloud server 130 by wire or wireless via the communication module 121. The cloud server 130 is communicated with the electronic device 140 via the internet, and the communication module 121 is electrically connected to alarm module 122.

In the embodiment, the processor 120 can be implemented by a microcontroller, a microprocessor, a digital signal processor, an application specific integrated circuit, a central processing unit, a control circuit and/or a graphics processing unit. The communication module 121 can be implemented by a global system for mobile communication, a personal handy-phone system, a long term evolution, a worldwide interoperability for microwave access, a wireless fidelity, etc. The alarm module 122 can be implemented by a buzzer, a light-emitting device or a combination can generate alert message in the form of sound or flash light.

The weight sensor 110 is configured to detect the weight of the object, such as the weight of drip bag or drip bottle but not limited thereof. The processor 120 is configured to receive the weight information which is detected by the weight sensor 110, and when the weight information is less than or equal to a drip threshold, the processor 120 is configured for sending an alert information to the alarm module 122.

The alarm module 122 is configured to receive the alert information and generating an alert sound or emitting an alert light. The communication module 121 is configured to transmit the real-time weight information detected by the weight sensor 110 to the cloud server 130 and to receive the setting information transmitted from the cloud server 130.

The cloud server 130 is configured to receive the weight information transmitted from the communication module 121 and compare the weight information with the setting information of the drip to calculate a time remaining. Afterwards, transmitting the remaining time to the electronic device 140 in real time. In the embodiment, the electronic device 140 can be implemented by a mobile device, a wearable device or a device received and emitted alert information.

Figure 2:
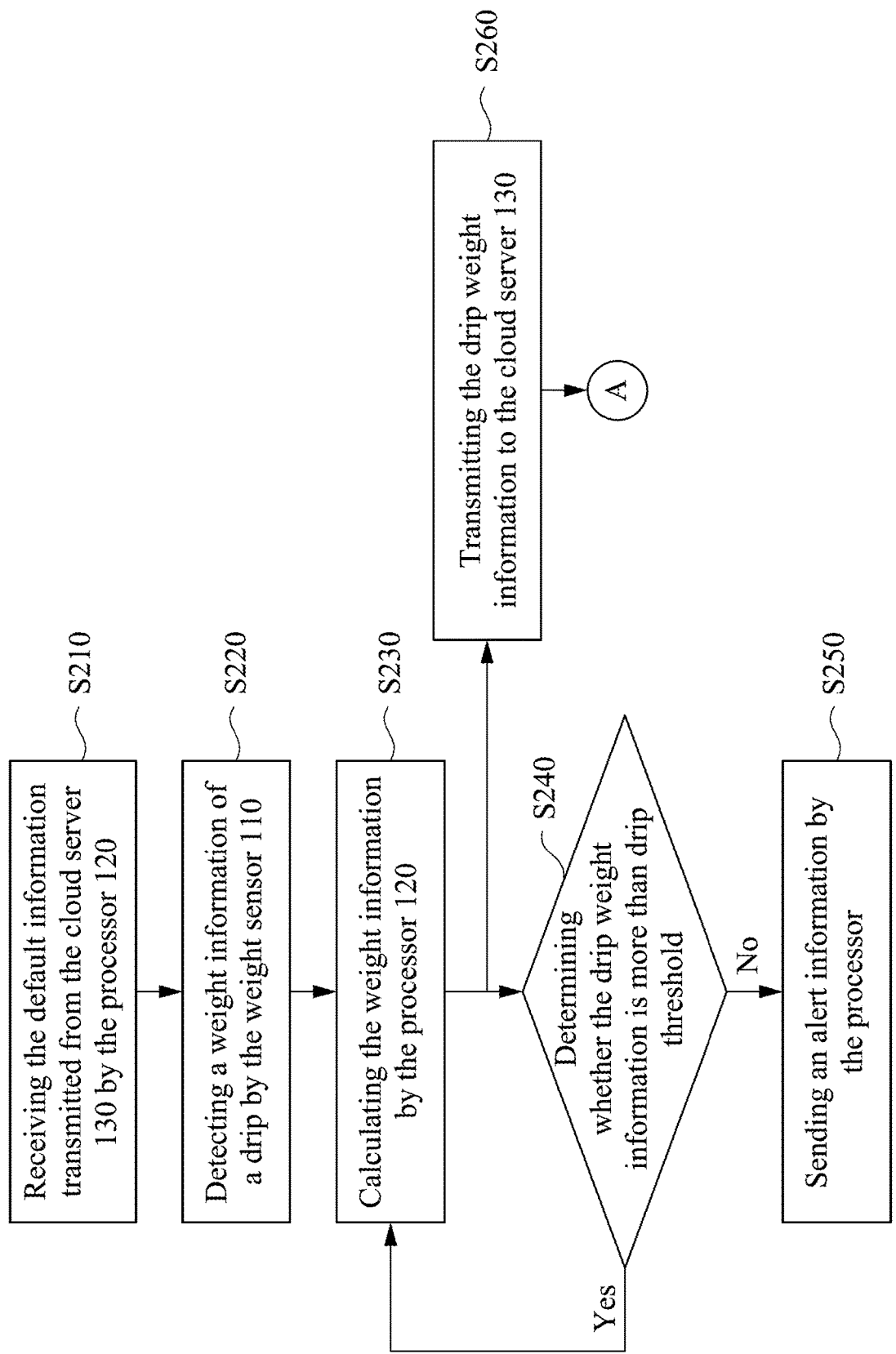
FIG. 2 is a flow diagram illustrating an intravenous drip real-time monitoring method according to an embodiment of the disclosure.
Figure 3:
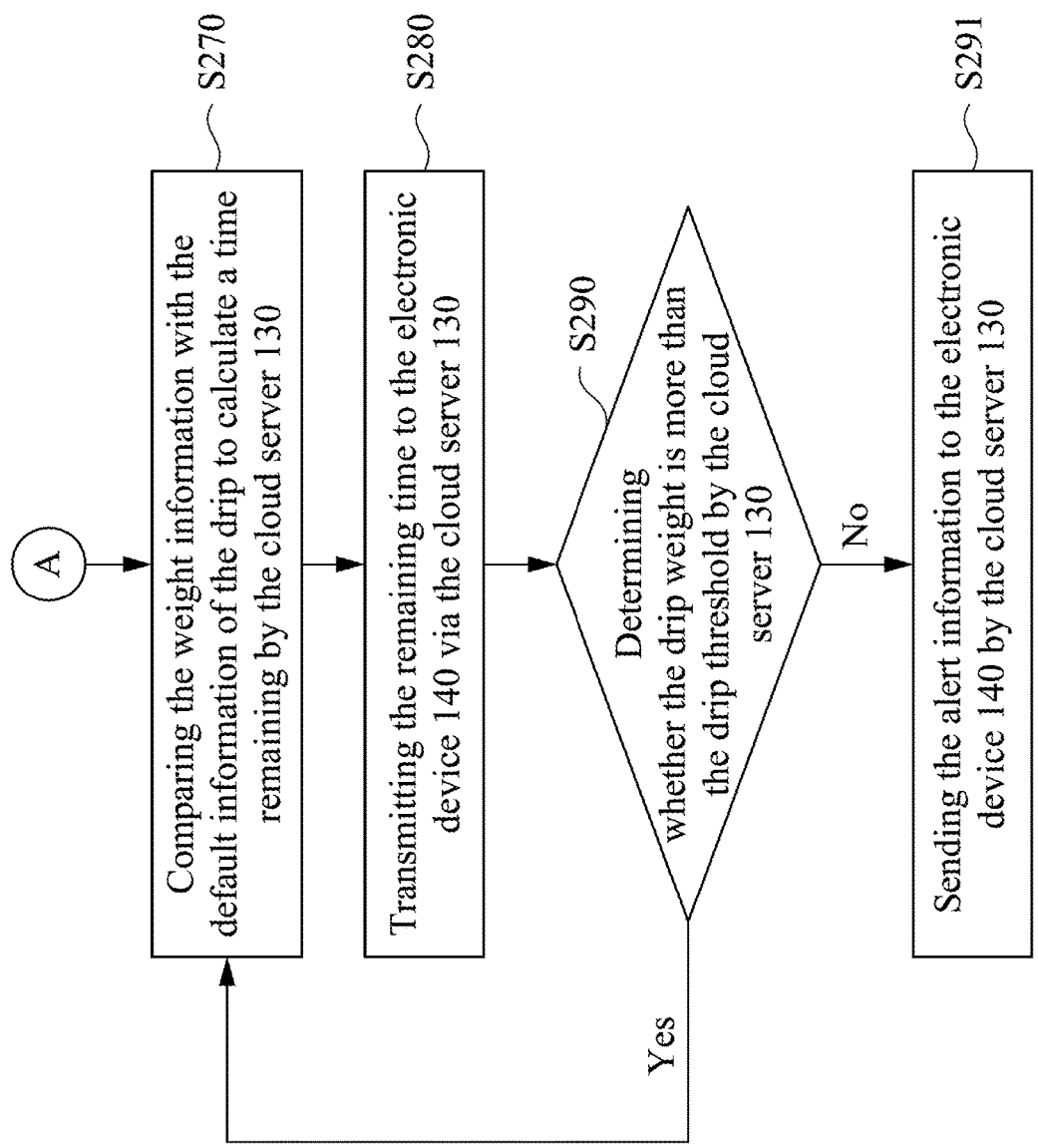
FIG. 3 is a flow diagram illustrating an intravenous drip real-time monitoring method according to an embodiment of the disclosure.

The operation of the intravenous drip monitoring system 100 is described in detail in accompany with FIG. 1, FIG. 2 and FIG. 3.

Reference is made to FIG. 2 and FIG. 3. FIG. 2 is a flow diagram illustrating an intravenous drip real-time monitoring method 200 according to an embodiment of the disclosure. FIG. 3 is a flow diagram illustrating an intravenous drip real-time monitoring method 200 according to an embodiment of the disclosure. The intravenous drip monitoring method 200 includes following steps (The steps are not retired in the sequence in which the steps are performed. That is, unless the sequence of the steps is interchangeable, and all or part of the steps may be simultaneously, partially simultaneously, or sequentially performed).

As the embodiment shown in FIG. 2, the intravenous drip monitoring method 200 firstly executes step S210 to receive the setting information transmitted from the cloud server 130 by the processor 120. In the embodiment, the cloud server 130 store the setting information of different drips, the setting information includes an empty drip bag weight, a drip threshold, a drip initial weight, a medicine type, a medicine brand, and a burette type, etc. When users install the intravenous drip real-time monitoring system 100 on drip, they may utilize the processor 120 to download the corresponding drip setting information from the cloud server 130 via the internet to control the weight sensor 110 according to the setting information.

Afterwards, the intravenous drip monitoring method 200 executes step S220 to detect a weight information of a drip by the weight sensor 110 and step S230 to calculate the weight information by the processor 120. In the embodiment, when the drip is installed the intravenous drip real-time monitoring system 100, the weight sensor 110 is configured to detect the weight of drip, and transmit the weight information to the processor 120. The processor 120 is configured to calculate the weight information from the weight sensor 110 continuously.

Afterwards, the intravenous drip monitoring method 200 executes step S240 and step S250 to determine whether the drip weight information is more than drip threshold, if not, sending an alert information by the processor. In the embodiment, the processor 120 is configured to detect whether the drip weight is less than or equal to the setting information continuously, once the drip weight information is less than or equal to the drip threshold, the processor 120 is configured to send the alert information to the alarm module 122.

Afterwards, the intravenous drip monitoring method 200 executes step S260 to transmit the drip weight information to the cloud server 130. In the embodiment, the processor 120 is configured to transmit the drip weight information to the cloud server 130 continuously, the drip data includes the drip weight, the condition of the alarm module 122 (e.g. monitoring condition or alert condition), the identification number of drip, the battery level of the processor 120, etc., and the cloud server 130 is configured to store the drip data in the memory.

Afterwards, the intravenous drip monitoring method 200 executes step S270 to compare the weight information with the setting information of the drip to calculate a time remaining by the cloud server 130. In the embodiment, the processor 120 is configured to transmit the drip weight information to the cloud server 130 real-time when the information is received. Then the cloud server 130 is configured to utilize the setting information to calculate the time remaining of drip. By comparing the initial drip weight and the real-time drip weight be able to calculate the remaining time of dripping. For example, the initial drip weight is 500 g, after a minute, the remaining weight is 490 g, and then the cloud server 130 can estimate the remaining time of dripping is 50 minutes.

Afterwards, the intravenous drip monitoring method 200 executes step S280 to transmit the remaining time to the electronic device 140 via the cloud server 130. Based on an aforesaid embodiment, after calculate the remaining time, the cloud server 130 is configured to transmit the remaining time (50 minutes) to the electronic device 140, and therefore, the holder of electronic device may aware the remaining time of dripping. In the embodiment, the electronic device 140 is installed reminding mechanism, for example, the electronic device 140 is configured to send alert information to remind the user (in this state may refer to nurse, caregiver or caretaker) to replace patient's drip.

Afterwards, the intravenous drip monitoring method 200 executes step S290 to determine whether the drip weight is more than the drip threshold by the cloud server 130 and step S291 if the drip weight is less than or equal to the drip threshold, sending the alert information to the electronic device 140 by the cloud server 130. In the embodiment, the cloud server 130 is configured to detect whether the drip weight is less than or equal to the drip threshold, once the drip weight is less than or equal to the drip threshold, the cloud server 130 is configured to transmit the remaining time of drip and the alert information to the electronic device 140. The cloud server 130 is configured to transmit the remaining time of drip and alert information to the corresponding electronic device 140 according to the identification number of drip included in the drip data. The alert information can be realized as reminding the caretaker replaces the patient's drip according to the alarm module condition.

In the embodiment, when the electronic device 140 is not connected to the cloud server 130, the electronic device 140 is configured to calculate the remaining time continuously. For example, when the electronic device 140 hold by the caregiver is not communicated with the internet, the electronic device 140 is not connected to the cloud server 130 real-time. Therefore, the electronic device 140 could not receive the remaining time transmitted by the cloud server 130. The electronic device 140 will activate the countdown mechanism and calculate the remaining time continuously, until the electronic device 140 is connected with the cloud server 130. The electronic device 140 will adjust the remaining time according to the remaining time the cloud server 130 calculated.

In the embodiment, in addition to receiving the drip data from the processor 120, the cloud server 130 can also receive the setting information of the drip. For example, the setting information of drip may change due to the update of the capacity of drugs, replace the company, or the drug certificate is expired, and therefore the drip setting can be updated by the user interface (not shown in figure) of the cloud server 130.

In the embodiment, the cloud server 130 can be utilized to record the patient's drip data. For example, even the disease is identical, the amount of drip may be different due to age, gender or race, such as a 20-30 years old white male and a 0-5 years old Asian female may need different amount of drip. The cloud server 130 can be utilized to collect the unrecognized personal data and provide the information to medical institution or medical college for researching.

Based on aforesaid embodiments, the intravenous drip real-time monitoring system and method are capable of improving the formerly intravenous drip monitoring system done by manual monitoring, utilizing the weight sensor to detect the weight of drip in real time and sending out an alert sound to caretaker remind him/her replace the drip when the drip weight is less than or equal to the threshold. The intravenous drip real-time monitoring system will also send the setting information to the cloud server and the cloud server transforms the drip weight to remaining time, and then it transmits the remaining time to the caregiver's electronic device to remind him/her to replace the drip in time. The setting information of drip transmitted from the cloud server to the intravenous drip real-time monitoring system. Therefore, the disclosure is able to achieve drip monitoring real-time and convenient setting up the drip monitoring device.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An intravenous drip real-time monitoring system, comprising:
    a weight sensor, configured for detecting a weight information of a drip;
    a processor electrically connected to the weight sensor, is configured for calculating the weight information, and when the weight information is less than a drip threshold, the processor is configured for sending an alert information; and
    a cloud server communicated with the processor, is configured for receiving the weight information transmitted from the processor, and comparing the weight information with a setting information of the drip to calculate a remaining time;
    wherein, the setting information comprises a weight of drip bag, the drip threshold, a drip initial weight, a medicine type, and a burette type.

2. The intravenous drip real-time monitoring system of claim 1, wherein the processor further comprising:
    a communication module, configured for receiving the setting information transmitted from the cloud server; and
    an alarm module, configured for receiving the alert information and generating a warning sound.

3. The intravenous drip real-time monitoring system of claim 1, wherein the processor and the cloud server are configured to determine the weight information is more than the drip threshold, if not, sending the alert information.

4. The intravenous drip real-time monitoring system of claim 1, wherein the setting information further comprises a medicine brand.

5. The intravenous drip real-time monitoring system of claim 1, further comprising an electronic device, communicated with the cloud server, is configured for receiving the remaining time transmitted from the cloud server.

6. The intravenous drip real-time monitoring system of claim 5, wherein when the electronic device is not connected to the cloud server, the electronic device is configured for calculating the remaining time continuously.

7. An intravenous drip real-time monitoring method, comprising:
- detecting a weight information of a drip by a weight sensor;
- calculating the weight information by a processor and when the weight information is less than a drip threshold, sending an alert information by the processor;
- transmitting the weight information to a cloud server by the processor; and
- comparing the weight information with a setting information of the drip to calculate a remaining time by the cloud server;
- wherein, the setting information comprises a weight of drip bag, the drip threshold, a drip initial weight, a medicine type, and a burette type.

8. The intravenous drip real-time monitoring method of claim 7, further comprising:
- receiving the setting information transmitted from the cloud server.

9. The intravenous drip real-time monitoring method of claim 7, wherein the processor and the cloud server are configured to determine the weight information is more than the drip threshold, if not, sending the alert information.

10. The intravenous drip real-time monitoring method of claim 7, further comprising: transmitting the remaining time to an electronic device by the cloud server, wherein when the electronic device is not connected to the cloud server, the remaining time is continuously calculated by the electronic device.

* * * * *